US006853449B2

(12) United States Patent
Hocker

(10) Patent No.: US 6,853,449 B2
(45) Date of Patent: Feb. 8, 2005

(54) PROGRAMMABLE DIFFRACTION GRATING SENSOR

(75) Inventor: G. Benjamin Hocker, Minnetonka, MN (US)

(73) Assignee: Honeywell International Inc., Morristown, NJ (US)

( * ) Notice: Subject to any disclaimer, the term of this patent is extended or adjusted under 35 U.S.C. 154(b) by 118 days.

(21) Appl. No.: 10/352,828

(22) Filed: Jan. 28, 2003

(65) Prior Publication Data

US 2004/0145737 A1 Jul. 29, 2004

(51) Int. Cl.⁷ .............................. G01J 3/18; G01J 3/457
(52) U.S. Cl. ................................. 356/328; 250/339.07
(58) Field of Search ............................... 356/326, 328; 250/339.07

(56) References Cited

U.S. PATENT DOCUMENTS

| | | |
|---|---|---|
| 4,557,603 A | 12/1985 | Oehler et al. |
| 4,818,882 A | 4/1989 | Nexo et al. |
| 4,866,681 A | 9/1989 | Fertig |
| 5,757,536 A | 5/1998 | Ricco et al. |
| 5,905,571 A | 5/1999 | Butler et al. |
| 5,933,245 A | 8/1999 | Wood et al. |
| 6,329,738 B1 | 12/2001 | Hung et al. |

OTHER PUBLICATIONS

Claspy, "Infrared Optoacoustic Spectroscopy and Detection" *Optoacoustic Spectroscopy and Detection*, 1977, Chapter 6, pp. 133–166.

Allan Rosencwaig, "Photoacoustic Spectrometers for Condensed Samples", *Photoacoustics and Photoacoustic Spectroscopy*, Chapter 12, pp. 137–157.

Dewey, Jr., "Opto–Acoustic Spectroscopy" *Optical Engineering–Nov. Dec. 1974*, vol. 13, No. 6, pp. 483–488.

Sourlier et al, "A Simple Device for Trace Gas Analyses in the Atmosphere", *Journal de Physique*, vol. 44, No. 10, Oct. 1983, pp. C6–587–C6–591.

Ulli et al, "Temperaturabhängiger Gasnachweis mit Metalloxid–Halbleitem", *Rapport de la reunion d'automne de la Societe Suisse de Physique*, vol. 54, 1981, pp. 631–636.

Sinclair et al, "Synthetic spectra: a tool for correlation spectroscopy" *Applied Optics*, vol. 36, No. 15, May 20, 1997, pp. 3342–3348.

Hocker et al, "The Polychromator: A Programmable MEMS Diffraction Grating for Synthetic Spectra" *Technical Digest 2000 Solid State Sensors and Actuator Workshop*, Hilton Head, SC, Jun. 4–8, 2000, pp. 89–92.

M.A. Butler et al., "A MEMS–based Programmable Diffraction Grating for Optical Holography in the Spectral Domain", IEEE International Electron Devices Meeting IEDM 2001; Washington, DC, US, Dec. 2–5 2001, 4 pp.

Proceedings of Space 2000: The Seventh International Conference and Exposition on Engineering, Construction, Operations, and Business in Space; Albuquerque, New Mexico, Feb. 27–Mar. 2, 2000, pp. 476–481.

C. Feifan et al., "Optical Model for Programmable Phase Grating Based on MOEMS", Proceedings of the Second International Symposium on Instrumentation Science and Technology; Aug. 18–22, 2002, Jinan, China, 6 pp.

Primary Examiner—F. L. Evans

(57) ABSTRACT

A programmable substance detector includes a light source, a sample cell, a programmable diffraction grating positioned to receive light from the light source and to direct diffracted light to the sample cell, and a detector associated with the cell to detect a match between a characteristic of the diffracted light and a corresponding characteristic of a substance within the cell.

33 Claims, 3 Drawing Sheets

PROGRAMMABLE DIFFRACTION GRATING SENSOR

This invention was made with Government support under Contract N660001-97-C-8620 awarded by the Defense Advanced Research Projects Agency/U.S. Navy. The Government has certain rights in the invention.

TECHNICAL FIELD OF THE INVENTION

The present invention relates to a sensor, such as a photoacoustic sensor, that may be programmed to detect selected substances such as gases.

BACKGROUND OF THE INVENTION

A spectrometer can be used to qualitatively and/or quantitatively analyze substances such as gases, liquids, and solids according to a spectral signature characteristic of each substance. A correlation spectrometer analyzes a sample of an unknown substance by first passing broadband light through the unknown substance so that the broadband light picks up the spectral signature of the unknown substance, and by then passing the light containing the spectral signature through a sample of a known target (reference) substance so that the transmitted light picks up the spectral signature of the target substance. The two spectral signatures are thereby correlated. If the correlation is sufficiently high, it may be assumed that the unknown substance and the target substance are the same.

The need for including a sample of a target substance limits the usefulness of the correlation spectrometer. It is awkward to change target substances. Moreover, the correlation spectrometry technique is impractical for transient substances because the target substance is unstable. This correlation spectroscopy technique is also impractical for detection of highly toxic substances because the use of a sample target substance is hazardous.

Therefore, known correlation spectrometers are, for the most part, still limited to the analysis of one or, in some instances, a very few substances because some form of mechanical programming is incorporated into the correlation spectrometers in order to provide the target signature. Such mechanical programming may be in the form of plural target gas cells, each of which must be filled with a sample of a different target gas, which gases may not be transient or highly toxic substances. Alternatively, the programming may take the form of spectral filters that are specifically designed and formed to transmit a spectral feature of the target substance, and must be precisely located. These filters are typically limited to utilize only a single one of the many spectral lines which characterize the target substance, and thus may fail to accurately distinguish the desired target substance from other substances.

Thus, prior art correlation spectrometers typically are preprogrammed for the analysis of a very limited number of substances, are not easily reprogrammed for the analysis of other substances, may not accurately distinguish the target substance, and are not practical for analysis of some classes of substances.

To solve some of these problems, it is also known to use a programmable diffraction grating in a correlation spectrometer where the diffraction grating may be programmed for the analysis of plural substances by generating a multi-line spectral signature characteristic of an unknown substance, thereby replacing the use of an actual sample of a target substance in a correlation spectrometer. The diffraction grating of this known correlation spectrometer may be electrically programmed in order to analyze one substance, and may be subsequently electrically reprogrammed in order to analyze another substance. Accordingly, the analysis of an unknown substance whose composition is not known beforehand may be performed by electrically programming the correlation spectrometer in order to optically correlate a spectral signature from an unknown sample substance with target spectral information about many different known target substances, where the target substance spectral information is stored electronically for use in electrically programming the diffraction grating.

Alternatively, a single diffraction grating may be designed to analyze a single target substance by generating a multi-line spectral signature characteristic of that target substance.

The programmable diffraction grating may be formed as a plurality of controllable grating elements in a multi-periodic spaced relationship so that a plurality of spectra can be detected by the correlation spectrometer. Such a diffraction grating may be formed on a substrate as an integrated device.

Known correlation spectrometers suffer from other drawbacks: expensive infrared detectors may have to be cooled well below room temperature to achieve the required sensitivity. Furthermore, such detectors must accurately measure very small changes in the light from the unknown sample transmitted through the programmable grating.

The present invention overcomes one or more of these or other problems by using a programmable diffraction grating between the light source and the sample cell rather than between the sample cell and the detector as is done in the prior art. Therefore, the programmable diffraction grating is part of the light source according to the present invention rather than part of the detector according to the prior art. A significant advantage of the invention is that it allows simple, sensitive photoacoustic detection.

As noted in prior art reference U.S. Pat. No. 5,933,245, herein incorporated by reference, photoacoustic measurement is based on the tendency of molecules, when exposed to certain frequencies of radiant energy (e.g. infrared radiant energy), to absorb the energy and reach higher levels of molecular vibration and rotation, thereby to reach a higher temperature and pressure. When the radiant energy is amplitude modulated, the resulting fluctuations in energy available for absorption produce corresponding temperature and pressure fluctuations.

A sensitive microphone can be used to generate an electrical output representing the pressure fluctuations. The amplitudes of the acoustic signal and resulting electrical output are proportional to the intensity of the radiation and the concentration value of the absorbing gas. Accordingly, given a constant amplitude of radiant energy illumination, the electrical output can be detected at the modulating frequency to provide a concentration value proportional to an absorbing amount of the gas. Further, the proportional relationship with light source intensity allows the user to increase sensitivity by increasing light source intensity. Thus the devices are well suited for measuring small concentration values of gases (ppm, i.e., parts-per-million range), especially as compared to sensors that rely on measurement of transmitted radiant energy.

A variety of these devices are known, e.g. see U.S. Pat. No. 4,557,603 (Oehler et al), U.S. Pat. No. 4,818,882 (Nexo et al), and U.S. Pat. No. 4,866,681 (Fertig), all of which are herein incorporated by reference. The devices have several components in common. In particular, a laser or other energy source produces radiant energy which is modulated either thermally (power on/off) or with a chopping device.

The modulated energy is provided to a cell containing a gas or gas mixture that absorbs the radiant energy, leading to temperature fluctuations in the gas that track the modulation frequency. Temperature is not sensed directly. Rather, pressure fluctuations that accompany the temperature fluctuations are detected by a sensitive microphone in the cell. The microphone output is detected at the modulation frequency, to provide an electrical signal proportional to the gas concentration.

Further discussion on these devices may be found in "Opto-Acoustic Spectroscopy", Dewey, Jr., Optical Engineering, November/December 1974, vol. 13, No. 6, pp. 483–488; "A Simple Device For Trace Gas Analyses In The Atmosphere", Journal De Physique, October 1983, pp. 587–591; "A simple photoacoustic gas-detection system", Rapport de la reunion d'autonne de la Societe Suisse de Physique, vol. 54, 1981, pp. 631–635; "Photoacoustics and Photoacoustic Spectroscopy," A. Rosencwaig, published by John Wiley&Sons(1980); and "Optoacoustic Spectroscopy and Detection," Y-H Pao, editor, published by Academic Press (1980, all herein incorporated by reference.

SUMMARY OF THE INVENTION

According to one aspect of the present invention, a programmable substance detector comprises a light source, an unknown substance within a cell, a programmable diffraction grating, and a detector. The programmable diffraction grating is positioned to receive light from the light source and to direct diffracted light to the unknown substance within the cell. The detector is associated with the cell containing the unknown substance and detects a match between the diffracted light and a substance within the cell.

According to another aspect of the present invention, a method of identifying a substance comprises the following: directing light through a first light path; diffracting the light from the first light path to produce a multi-line spectrum of diffracted light uniquely associated with a target substance; supplying the diffracted light having the multi-line spectrum through a second light path to an unknown substance; and, identifying the unknown substance as the target substance based on the multi-line spectrum of the diffracted light.

According to still another aspect of the present invention, a programmable substance detector comprises a light source, a photoacoustic cell, a programmable diffraction grating, and a microphone. The programmable diffraction grating is positioned to receive light from the light source, to diffract the received light, to modulate the diffracted received light at a modulation frequency, and to direct the modulated diffracted light to the photoacoustic cell. The microphone is associated with the photoacoustic cell and detects an acoustic signal at the modulation frequency caused by a match between a characteristic of the diffracted light and a corresponding characteristic of an unknown substance within the cell.

BRIEF DESCRIPTION OF THE DRAWINGS

These and other features and advantages will become more apparent from a detailed consideration of the invention when taken in conjunction with the drawings in which.

DETAILED DESCRIPTION

Figure 1:
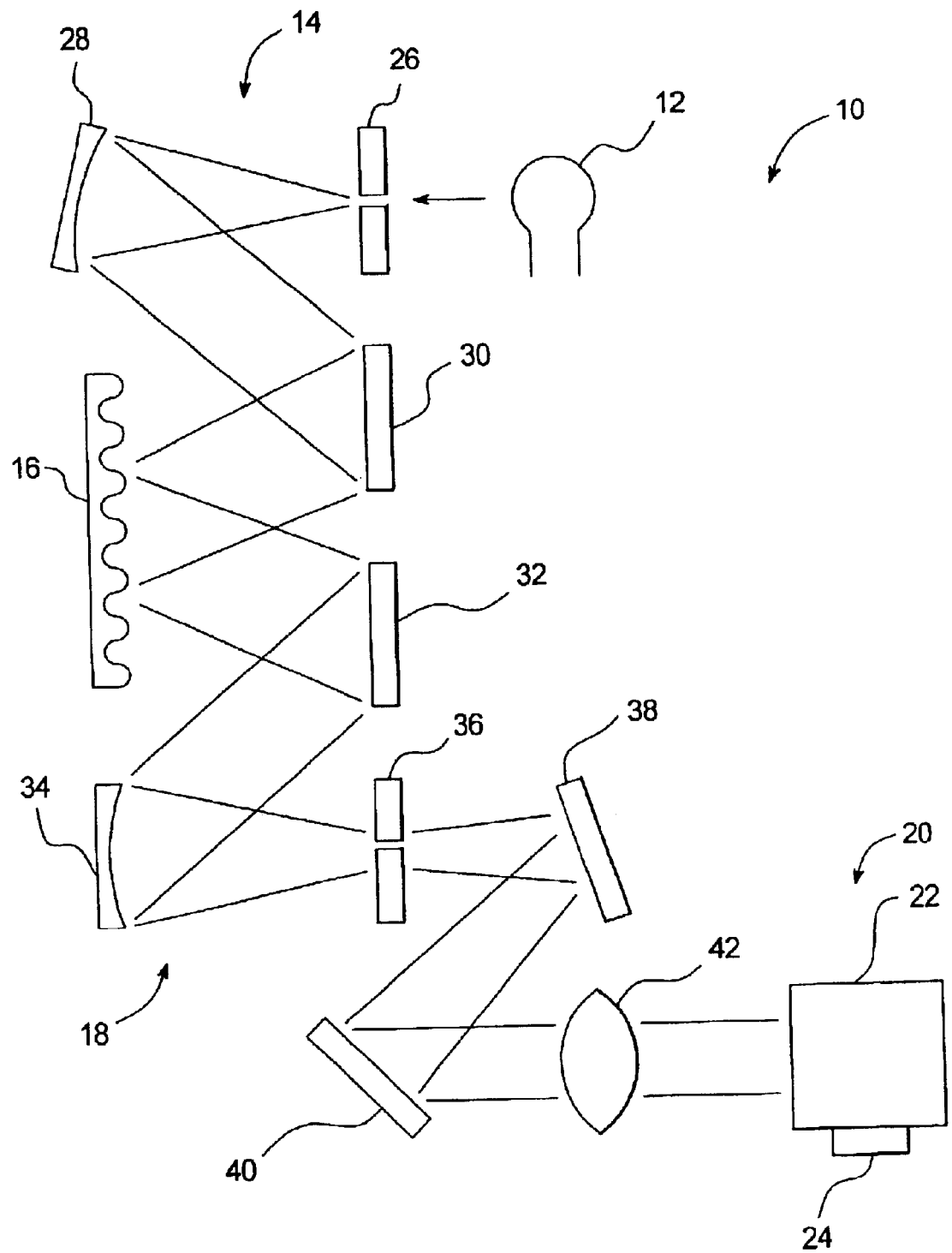
FIG. 1 shows a programmable substance detector having a programmable diffraction grating light source according to an embodiment of the present invention.

A programmable substance detector 10 according to an embodiment of the present invention is shown in FIG. 1 and includes a light source 12. The light source 12, for example, may be a source of infrared light. The light from the light source 12 is directed along a first light path 14 to a programmable diffraction grating 16. The programmable diffraction grating 16 is controlled so as to diffract light having a multi-line spectra characteristic of a target substance. The programmable diffraction grating 16 also suitably modulates the light from the light source 12 at a predetermined modulation frequency. The diffracted and modulated light from the programmable diffraction grating 16 is supplied through a second light path 18 to a sample cell 20 holding a sample of an unknown substance, such as a gas, to be identified. The modulation imposed by the programmable diffraction grating 16 may be, for example, amplitude modulation. Alternatively, the modulation may be imposed by a separate mechanism, such as by an optical chopper.

The advantage of using the programmable diffraction grating 16 is that it may be sequentially programmed so that the light it directs to the second light path 18 contains sequential corresponding multi-line spectra, where each multi-line spectrum is representative of a corresponding known target substance. Accordingly, the programmable diffraction grating 16 may be programmed so that the light it directs to the second light path 18 contains a first multi-line spectrum representative of a first known target substance, the programmable diffraction grating 16 may then be programmed so that the light it directs to the second light path 18 contains a second multi-line spectrum representative of a second known target substance, and so on until the substance in the sample cell 20 is identified.

The sample cell 20, for example, may be a photoacoustic cell 22 having a microphone 24 attached thereto or otherwise associated therewith. When the substance within the sample cell 20 matches the known target substance whose multi-line spectrum is contained in the light directed from the programmable diffraction grating 16 into the sample cell 20, the photoacoustic cell 22 generates an acoustic signal at the modulation frequency. This signal is detected by the microphone 24 to indicate the presence of a sample substance that matches the known target substance whose multi-line spectrum is currently being generated by the programmable diffraction grating 16. Therefore, the sample of the substance in the sample cell 20 may be identified as the known target substance.

Accordingly, the programmable diffraction grating 16 is programmed so that the light it directs to the second light path 18 contains a first multi-line spectrum representative of a first known target substance. If the substance contained within the photoacoustic cell 22 is not the first known target substance, the microphone 24 attached to the sample cell 20 does not detect a signal at the modulation frequency. Therefore, the programmable diffraction grating 16 is programmed so that the light it directs to the second light path 18 contains a second multi-line spectrum representative of a second known target substance. If the substance contained within the photoacoustic cell 22 is not the second known target substance, the microphone 24 attached to the sample cell 20 again does not detect a signal at the modulation frequency. This process is repeated until the substance contained within the photoacoustic cell 22 matches one of the known target substances, at which time the microphone 24 attached to the photoacoustic cell 22 detects a signal at the modulation frequency.

The first and second light paths 14 and 18 may contain various optical elements such as slits, mirrors, lenses, and/or filters as are known in correlation spectrometers. For example, the first light path 14 may contain a slit 26, a mirror 28, and a mirror 30, and the second light path 18 may contain a mirror 32, a mirror 34, a slit 36, a mirror 38, a mirror 40, and a lens 42. The first light path 14 collimates and directs the light from the light source 12 to the programmable diffraction grating 16. The programmable diffraction grating 16 generates a desired synthetic multi-line spectrum in a diffracted beam having the predetermined modulation frequency. The second light path 18 then collimates and directs the light from the programmable diffraction grating 16 to the sample cell 20.

This set of optical elements is representative only of one possible configuration. A variety of optical elements designs and configurations are apparent to one skilled in the art. Other configurations may contain fewer elements or may contain additional elements, while still accomplishing the desired function of directing light along the first and second paths.

The programmable diffraction grating 16, for example, may be of the type disclosed in U.S. Pat. No. 5,757,536 and/or U.S. Pat. No. 5,905,571 and/or U.S. Pat. No. 6,329,738, all herein incorporated by reference. Generally, the programmable diffraction grating 16 may be fabricated by polysilicon surface micromachining. Two polysilicon layers may be used for electrical interconnections and actuating electrodes, and two polysilicon layers may be used for the actuated structure.

Figure 2:
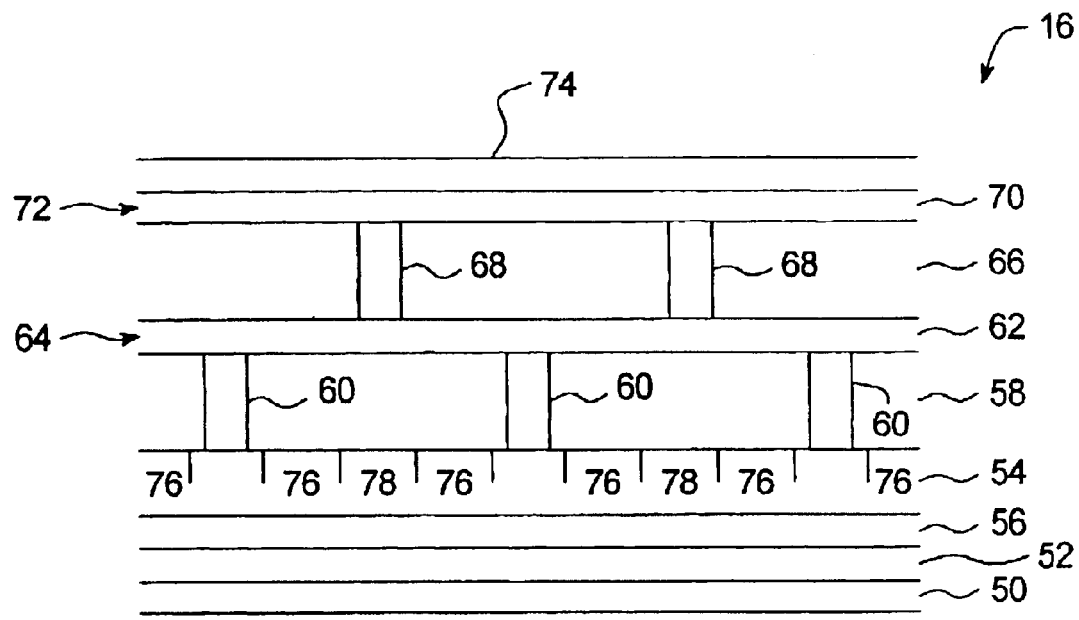
FIGS. 2 and 3 are side views of a known programmable diffraction grating that can be used in the programmable substance detector of FIG. 1.

First, FIG. 2 shows a known programmable diffraction grating, a thermal oxide layer 50 is grown on an ultra-flat silicon wafer. Two layers 52 and 54 of boron doped polysilicon separated by a silicon nitride layer 56 are deposited and are formed as the interconnection and actuating electrode structures for the individual control of each of the bending and mirror beams of the programmable diffraction grating 16. A relatively thick first sacrificial layer 58 of silicon dioxide is deposited and will define a free-space actuation gap between the bending beams and the electrodes. Vias are patterned and etched through the first sacrificial layer 58 so that first support posts 60 are formed as a bending beam polysilicon layer 62 is deposited. The first support posts 60 will support the bending beams. Small dimples may be etched in the first sacrificial layer 58 and will cause nodules to form on the bottom of the bending beam polysilicon layer 62 to prevent striction during operation should the bending beam pull in.

The bending beam polysilicon layer 62 is deposited, implanted, and patterned to form a plurality of parallel bending beams. Each bending beam may be controlled by a corresponding actuating electrode. The edge of one of the bending beams 64 is shown in FIG. 2, and the other bending beams are behind (and/or in front of) the bending beam 64 shown in FIG. 2. A second sacrificial layer 66 of silicon dioxide is deposited over the bending beam polysilicon layer 62. Vias are patterned and etched through the second sacrificial layer 66 so that second support posts 68 are formed when a top mirror beam polysilicon layer 70 is deposited.

The top mirror beam polysilicon layer 70 is deposited, implanted, and patterned to form a plurality of parallel mirror beams 72 each of which overlies a corresponding one of the bending beams 64. The edge of one of the mirror beams 72 is shown in FIG. 2, and the other mirror beams are behind (and/or in front of) the mirror beam 72 shown in FIG. 2.

A typical thickness for each of the bending and top mirror beam layers 62 and 70 and the first and second sacrificial layers 58 and 66 is approximately 2 microns. The wafer is annealed to set the polysilicon stress, a reflective material 74 such as gold is deposited on the mirror beams 72, and the first and second sacrificial layers 58 and 66 are removed.

The post to post distances between the first support posts 60 and between the second support posts 68 may be on the order to 500 to 700 microns, and the lengths of the actuating electrodes 76 and the ground electrodes 78 may be on the order of 80 to 100 microns.

Figure 3:
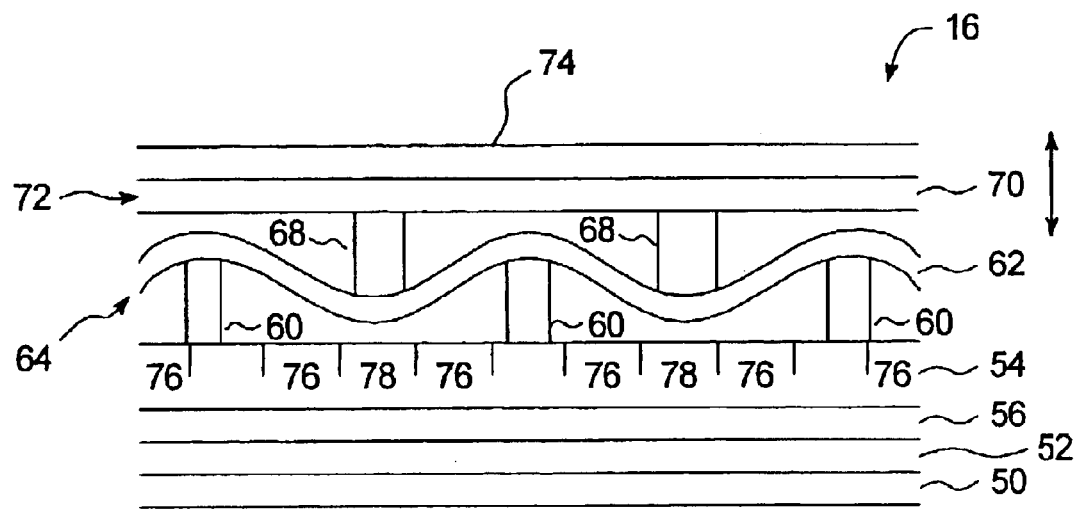

As shown in the side view of FIG. 2, the bending beam 64 of the programmable diffraction grating 16 is not bending. As shown in the side view of FIG. 3, the bending beam 64 of the programmable diffraction grating 16 is bending due to actuation. As each of the bending beams 64 bends and unbends as shown in FIGS. 2 and 3, the corresponding mirror beam 72 is displaced vertically in the direction of the arrow of FIG. 3. It is this movement that causes the diffraction of the light from the light source 12.

The programmable diffraction grating 16 may have 1024 individually addressable diffractive elements, i.e., mirrors, that can be individually positioned by the bending beams 64 to generate corresponding synthetic spectra where each spectra corresponds to a known target substance. Each diffractive element may be on the order of 10 microns wide and 1 centimeter long. (However, the dimensions given herein are exemplary and may be varied. Also, FIGS. 2 and 3 are not drawn to scale.) These diffraction elements may be controlled in groups, if desired, for ease of patterning control signal lines to the actuating electrodes.

It is generally known how drive voltages may be designed to generate the desired multi-line spectrum from the above-identified references, including U.S. Pat. No. 5,905,571

Figure 4:
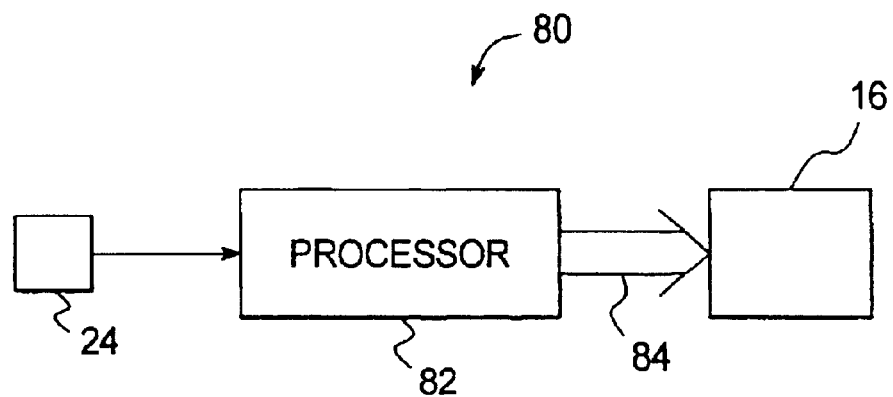
FIG. 4 shows an exemplary control system that may be used to control the programmable diffraction grating of FIG. 1 in order to identify an unknown substance in a sample cell; and, FIG. 5 is a flow chart illustrating the operation of the processor of the control system shown in FIG. 4.

A control system 80 is shown in FIG. 4 and controls the programmable diffraction grating 16 so that the multi-line spectra corresponding to known target substances may be sequentially generated until a substance in the photoacoustic cell 22 is identified. The control system 80 includes a processor 82 that has an input coupled to the microphone 24 of the photoacoustic cell 22 and that has a plurality of drive lines 84 that supply individual and/or group drive signals to the actuating electrodes of the programmable diffraction grating 16 so as to generate a different multi-line spectrum for each different set of drive signals supplied by the processor 82. These drive signals may be modulated at the predetermined modulation frequency as discussed above.

Figure 5:
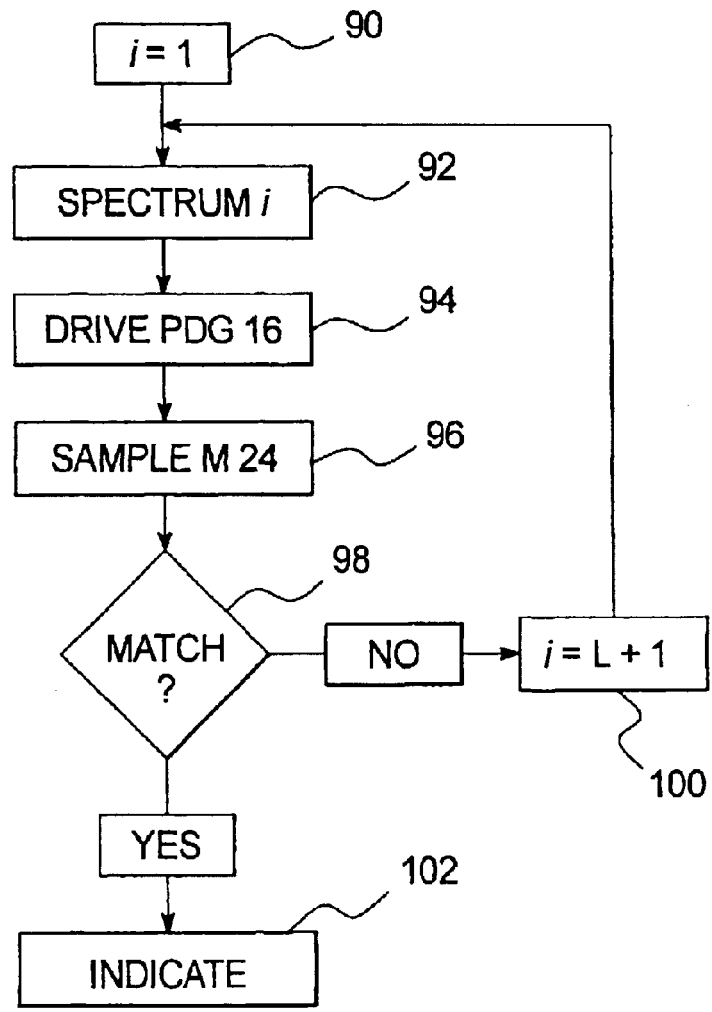

The processor 82 may operate in accordance with the flow chart illustrated in FIG. 5. As shown in FIG. 5, the processor 82, at a block 90, sets a variable i to one and, at a block 92, fetches from memory a first set of drive lines 84 over which drive signals are to be supplied by the processor 82 that will cause the programmable diffraction grating 16 to generate a multi-line spectrum of light according to a first known target substance. The processor 82 at a block 94 modulates these drive signals according to the predetermined modulation frequency and supplies the modulated drive signals to the programmable diffraction grating 16 over the selected first set of drive lines 84 in order to generate the multi-line spectrum of light according to the first known target substance. At a block 96, the processor 82 samples the output of the microphone 24 and determines at a block 98 whether the microphone 24 has detected an acoustic signal at the predetermined modulation frequency, i.e., the processor 82 determines whether the first known target substance and the unknown substance in the photoacoustic cell 22 match.

If the microphone 24 has not detected an acoustic signal at the predetermined modulation frequency, the processor at a block 100 increments the variable i by one and returns to the block 92 to fetch from memory a second set of the drive lines 84 over which drive signals are to be supplied by the processor 82 that will cause the programmable diffraction grating 16 to generate a multi-line spectrum of light according to a second known target substance. The processor 82 at the block 94 modulates these drive signals according to the predetermined modulation frequency and supplies the modulated drive signals to the programmable diffraction grating 16 over the second set of drive lines 84 in order to generate the multi-line spectrum of light according to the second known target substance. At the block 96, the processor 82 samples the output of the microphone 24 and determines at the block 98 whether the microphone 24 has detected an acoustic signal at the predetermined modulation frequency.

If the microphone 24 again has not detected an acoustic signal at the predetermined modulation frequency, the processor at the block 100 increments the variable i by one and program flow returns to the block 92. This process is repeated until the processor 82 at the block 98 determines that the known target substance, which corresponds to the current value of i, and the unknown substance in the photoacoustic cell 22 match, at which point the processor 82 provides an indication at a block 102 that the unknown substance in the photoacoustic cell 22 is the known target substance corresponding to the current value of i.

Certain modifications of the present invention may have been discussed above. Other modifications will occur to those practicing in the art of the present invention. For example, the sample cell 20 need not comprise the photoacoustic cell 22 and the microphone 24. Instead, the sample cell 20 may comprise a cell that passes the light from the second light path 18 through to a photodetector. Accordingly, if the unknown substance within the cell absorbs the light from the second light path 18, because the multi-line spectrum of the light from the second light path 18 matches the multi-line spectrum of the unknown substance in the cell, the photodetector will detect a change in the light passing through the cell. Other types of cell and detector combinations may also be used.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

I claim:
1. A programmable substance detector comprising:
   a light source;
   a sample cell;
   a programmable diffraction grating positioned to receive light from the light source and to direct diffracted light to the sample cell; and,
   a detector associated with the cell to detect a match between the diffracted light and a substance within the cell.

2. The programmable substance detector of claim 1 further comprising a controller, wherein the controller is arranged to control the programmable diffraction grating to generate a plurality of multi-line spectra, and wherein each of the multi-line spectra corresponds to a different known target substance.

3. The programmable substance detector of claim 2 wherein the sample cell comprises a photoacoustic cell and a microphone associated with the photoacoustic cell.

4. The programmable substance detector of claim 3 wherein the controller is arranged to modulate the light emitted by the programmable diffraction grating at a modulation frequency, and wherein the microphone detects an acoustic signal at the modulation frequency when an unknown substance within the photoacoustic cell matches one of the known target substances.

5. The programmable substance detector of claim 4 wherein the programmable diffraction grating comprises a plurality of individually controllable diffraction elements.

6. The programmable substance detector of claim 1 wherein the sample cell comprises a photoacoustic cell and a microphone associated with the photoacoustic cell.

7. The programmable substance detector of claim 6 wherein the microphone detects an acoustic signal when the diffracted light matches an unknown substance within the photoacoustic cell.

8. The programmable substance detector of claim 7 wherein the programmable diffraction grating comprises a plurality of individually controllable diffraction elements.

9. The programmable substance detector of claim 1 wherein the sample cell comprises a cell and a light detector associated with the cell.

10. The programmable substance detector of claim 9 wherein the light detector detects a decrease in light from the cell when an unknown substance within the cell matches one of the known target substances.

11. The programmable substance detector of claim 1 wherein the programmable diffraction grating comprises a plurality of individually controllable diffraction elements.

12. The programmable substance detector of claim 1 wherein the light source comprises an infrared light source.

13. A method of identifying a substance comprising:
   directing light through a first light path;
   diffracting the light from the first light path to produce a multi-line spectrum of diffracted light uniquely associated with a target substance;
   supplying the diffracted light having the multi-line spectrum through a second light path to an unknown substance; and,
   identifying the unknown substance as the target substance based on the multi-line spectrum of the diffracted light.

14. The method of claim 13 wherein the diffracting of the light from the first light path to produce a multi-line spectrum of diffracted light comprises diffracting the light from the first light path to produce a plurality of multi-line spectra, wherein each of the multi-line spectra corresponds to a different known target substance, and wherein the identifying of the unknown substance based on the multi-line spectrum of the diffracted light comprises identifying the unknown substance based on one of the multi-line spectra.

15. The method of claim 14 wherein the identifying of the unknown substance based on one of the multi-line spectra comprises photoacoustically identifying the unknown substance based on one of the multi-line spectra.

16. The method of claim 15 wherein the diffracting of the light from the first light path to produce multi-line spectra comprises modulating the light at a modulation frequency to produce multi-line spectra of modulated diffracted light, wherein the supplying of the diffracted light having the multi-line spectrum through a second light path comprises supplying the modulated diffracted light through the second light path, and wherein the identifying of the unknown substance based on one of the multi-line spectra comprises detecting an acoustic signal at the modulation frequency.

17. The method of claim 16 wherein the diffracting of the light from the first light path to produce multi-line spectra comprises diffracting the light from the first light path by use of a plurality of individually controllable diffraction elements.

18. The method of claim 13 wherein the identifying of the unknown substance based on the multi-line spectrum comprises photoacoustically identifying the unknown substance based on the multi-line spectrum.

19. The method of claim 18 wherein the diffracting of the light from the first light path to produce a multi-line spectrum comprises modulating the light according to a modulation frequency to produce a multi-line spectrum of modulated diffracted light, wherein the supplying of the diffracted light having the multi-line spectrum through a second light path comprises supplying the modulated diffracted light through the second light path, and wherein the identifying of the unknown substance based on the multi-line spectrum comprises detecting an acoustic signal at the modulation frequency.

20. The method of claim 19 wherein the diffracting of the light from the first light path to produce a multi-line spectrum of diffracted light comprises diffracting the light from the first light path by use of a plurality of individually controllable diffraction elements.

21. The method of claim 13 wherein the diffracting of the light from the first light path to produce a multi-line spectrum comprises modulating the light according to a modulation frequency to produce a multi-line spectrum of modulated diffracted light, wherein the supplying of the diffracted light having the multi-line spectrum through a second light path comprises supplying the modulated diffracted light through the second light path, and wherein the identifying of the unknown substance based on the multi-line spectrum comprises detecting a signal at the modulation frequency.

22. The method of claim 21 wherein the diffracting of the light from the first light path to produce a multi-line spectrum of diffracted light comprises diffracting the light from the first light path by use of a plurality of individually controllable diffraction elements.

23. The method of claim 13 wherein the diffracting of the light from the first light path to produce a multi-line spectrum of diffracted light comprises diffracting the light from the first light path by use of a plurality of individually controllable diffraction elements.

24. The method of claim 13 wherein the light source comprises an infrared light source.

25. The method of claim 13 wherein the diffracting of the light from the first light path to produce a multi-line spectrum comprises diffracting and modulating the light according to a modulation frequency.

26. The method of claim 13 wherein the identifying of the unknown substance comprises identifying the unknown substance as the target substance based on a reduction in light emerging from the unknown substance.

27. A programmable substance detector comprising:

a light source;

a photoacoustic cell;

a programmable diffraction grating positioned to receive light from the light source, to diffract the received light, to modulate the diffracted received light at a modulation frequency, and to direct the modulated diffracted light to the photoacoustic cell; and, a microphone associated with the photoacoustic cell to detect an acoustic signal at the modulation frequency caused by a match between a characteristic of the diffracted light and a corresponding characteristic of an unknown substance within the cell.

28. The programmable substance detector of claim 27 wherein the programmable diffraction grating is arranged to diffract the received light so as to produce a multi-line spectrum.

29. The programmable substance detector of claim 28 further comprising a controller, wherein the controller is arranged to control the programmable diffraction grating to generate a plurality of multi-line spectra, and wherein each of the multi-line spectra corresponds to a different known target substance.

30. The programmable substance detector of claim 29 wherein the microphone detects an acoustic signal at the modulation frequency when an unknown substance within the photoacoustic cell matches one of the known target substances.

31. The programmable substance detector of claim 30 wherein the programmable diffraction grating comprises a plurality of individually controllable diffraction elements.

32. The programmable substance detector of claim 27 wherein the programmable diffraction grating comprises a plurality of individually controllable diffraction elements.

33. The programmable substance detector of claim 27 wherein the light source comprises an infrared light source.

* * * * *